United States Patent [19]

Schopflin et al.

[11] 4,230,686

[45] Oct. 28, 1980

[54] DRUG EXCIPIENT OF SILICONE RUBBER

[75] Inventors: Gisela Schopflin; Peter Fuchs, both of Berlin; Karl H. Kolb, Holzhausen, all of Fed. Rep. of Germany

[73] Assignee: Schering Aktiengesellschaft, Berlin and Bergkamen, Fed. Rep. of Germany

[21] Appl. No.: 753,876

[22] Filed: Dec. 23, 1976

Related U.S. Application Data

[60] Continuation of Ser. No. 563,233, Mar. 28, 1975, abandoned, which is a division of Ser. No. 444,886, Feb. 22, 1974, abandoned, which is a continuation-in-part of Ser. No. 307,940, Nov. 20, 1972, abandoned.

[30] Foreign Application Priority Data

Nov. 20, 1971 [DE] Fed. Rep. of Germany ....... 2158226

[51] Int. Cl.$^2$ .......................... A61K 9/22; A61K 9/26
[52] U.S. Cl. ........................................ 424/22; 128/260
[58] Field of Search ................................... 424/19–22, 424/32, 70; 260/825, 46.50 A, 46.55

[56] References Cited

U.S. PATENT DOCUMENTS

| | | | |
|---|---|---|---|
| 2,823,218 | 2/1958 | Speir et al. | 260/825 |
| 3,020,260 | 2/1962 | Nelson | 260/46.5 UA |
| 3,127,363 | 3/1964 | Nitzsche et al. | 260/825 |
| 3,220,972 | 11/1965 | Lamoreaux | 260/825 |
| 3,279,996 | 10/1966 | Long et al. | 424/32 X |
| 3,699,073 | 10/1972 | Wada et al. | 260/46.5 UA |

*Primary Examiner*—Shep K. Rose
*Attorney, Agent, or Firm*—Millen & White

[57] ABSTRACT

Nontoxic sustained release pharmaceutical compositions containing one or more nonionic, lipophilic drugs in a cured low temperature vulcanizable (LTV) silicone elastomer excipient are prepared substantially free of toxic vulcanizing agents or drug-reactive by-products in the elastomeric material by curing an admixture of the drug or drug containing core, LTV-methylvinylsiloxane units containing linear dimethylpolysiloxane and a dimethylpolysiloxane crosslinking composition containing silicon linked H atoms using a noble metal-based catalyst. The resultant compositions are characterized by good physical properties and a constant rate of drug release in the body over long periods of time.

16 Claims, No Drawings

DRUG EXCIPIENT OF SILICONE RUBBER

This is a continuation, of application Ser. No. 563,233, filed Mar. 28, 1975, which is a Continuation of application Ser. No. 444,886 filed Feb. 22, 1974 which in turn is a Continuation-in-Part of application Ser. No. 307,940 filed Nov. 20, 1972, all now abandoned.

BACKGROUND OF THE INVENTION

This invention relates to silicone rubber drug excipients having a regular, uniform and prolonged drug dispensation rate and medicines prepared with such excipients.

Organopolysiloxane elastomers are known to be suitable vehicles for depot drug preparations for long-term treatment in a living organism, since they are neither decomposed nor resorbed by the organism and exhibit good tissue compatibility in comparison with other synthetic polymers.

Nonionic, lipid-soluble drugs occluded in organopolysiloxane elastomers are delay released from the vehicle are described in Kincl et al., Steroids 11 (5):675–680 (1968); Dzuik and Cook, Endocrinology 78: 208–211 (1966); Garrett and Chemburkar, J. Pharm. Sci. 57: 1401–1409 (1968).

Nonionic, lipophilic active drug agents are soluble in organopolysiloxane elastomers, the degree of solubility depending on the type of silicone elastomer. Consequently, the rate at which the drug is released from the silicone rubber vehicle depends substantially on the composition of this vehicle. The organic substituents in the polysiloxane employed must be selected so that no undesired side effects occur due to the presence of the polymer in the organism.

The use of solid organopolysiloxane elastomers as drug excipients for controllable release of effective agents is known and has been described, inter alia, in U.S. Pat. No. 3,279,996; British Pat. No. 998,794; and German Published Unexamined Application Nos. 1,912,343; 1,900,196; and 1,467,861.

The following organopolysiloxane elastomer raw materials are customary for the preparation of drug excipients:

Thermosetting organopolysiloxanes which are to be cured with peroxide catalysts, e.g., benzoyl peroxide or di-p-chlorobenzoyl peroxide, at temperatures of about 200° C., and which require a heat aftertreatment; such organopolysiloxanes can be produced, for example, in accordance with U.S. Pat. Nos. 2,541,137; 2,890,188; 2,723,966; 2,863,846; and 3,002,951.

Furthermore, hydroxyl-terminated organopolysiloxanes of the room temperature vulcanizing (RTV) type have been employed which, after the addition of cross-linking agents in the presence of curing catalysts, harden at room temperature under atmospheric humidity into elastomers. Typical curing catalysts are metallic salts of a carboxylic acid, preferably tin salts, e.g., tin(II) octoate and tin(II)-2-ethylhexanoate.

One-component silicone rubber materials have also been used which set at room temperature under atmospheric humidity without any further additive. These one-component substances contain primarily organopolysiloxanes with two terminal-positioned acyloxy groups, e.g., acetoxy; the acyloxy groups are hydrolyzed under atmospheric humidity to form tri-functional siloxane units which cross-link the polymer into a cured elastomer. These organopolysiloxanes can be prepared, for example, according to U.S. Pat. Nos. 2,927,907 and 3,035,016, and British Pat. Nos. 798,669 and 804,199.

These latter polysiloxane elastomers are obtained by thermosetting linear organopolysiloxanes and are utilized only in the preformed vulcanized condition to prepare drug excipients. Vulcanization of organopolysiloxane containing the drug is impossible, since almost all useful drugs are unstable either at the required high vulcanizing temperature and/or in the presence of peroxide catalysts.

Capsule-shaped drug excipients of silicone rubber are known from the literature and have been described by Folkman and Long, JSR, VI (3): 139–142 (1966); Dzuik and Cook, Endocrinology 78: 208–211 (1966); Sundaram and Kincl, Steroids 12 (4): 517–524 (1968); Kratochvil et al., Steroids 15 (4): 505–513 (1970); and Croxatto et al., Amer. J. Obstet. Gyn. 105: 1135–1138 (1969).

These excipients are prepared by cementing the open ends of silicone rubber tubing into which the effective drug has been filled. A one-component silicone rubber material which sets at room temperature, e.g., RTV-silicone glue, is customarily employed for cementing purposes. Such capsule-like drug excipients cannot, however, be produced in satisfactory uniformity and numbers according to the process disclosed in the aforementioned German Published Unexamined Application No. 1,912,343. Furthermore, drug vehicles prepared from a silicone rubber tube by cementing with RTV-silicone glue have the disadvantage that the desirably high, prolonged regular release of effective agent from the carrier material cannot be attained. During the period of use, the packing density of the drug in the interior of the capsule is reduced, causing a marked reduction of the already relatively irregular release rate of effective agent. The irregular release rate of effective agent is compounded by the use of two differently structured types of silicone rubber as the vehicle for the effective drug agent. Customarily, the RTV-silicone adhesives utilized are cured at room temperature and under atmospheric humidity with acetic acid being split off, and the acetic acid vulcanization by-product can enter into undesired reactions with the drug. A further disadvantage of the above-described drug capsules is the poor mechanical properties of the slicone elastomer carrier material at the points of cementing.

The use of RTV-silicone rubber one-component materials alone is virtually impossible because they cannot be vulcanized in the layer thickness necessary for suitably strong excipients within a reasonable period of time and toxic by-products of the vulcanization process can adhere to the vulcanized product for an undesirably long period of time; the drugs are often unstable in the presence of these by-products.

By means of two-component RTV-type silicone rubber compositions which are cured to elastomers at room temperaure, drug excipients can be constructed according to the matrix principle in a technically simple manner. However, since the RTV-silicone rubber two-component compositions set to elastomers only in the presence of atmospheric humidity, these matrices cannot be produced in all desired shapes. Furthermore, many of the carboxylic acid metal salts customary as vulcanization accelerators are toxic to a living organism, as are the RTV-vulcanizates prepared therewith.

Silicone rubber vulcanizates can be produced in a hardness range of from 20 to 90 Shore A (DIN 53 505). As is known, vulcanizates of 45 to 70 Shore A exhibit the most favorable mechanical properties for use as a pharmaceutical excipient. However, the elastomers obtained from RTV-silicone rubber two-component mixtures exhibit only a hardness of 27-28 Shore A, and disintegrate into crumbs when subjected to only a slight to moderate mechanical stress. The loss of the original shape of the vehicle is then accompanied by an immediate and undesirable accelerated rate of drug release from the carrier material. Furthermore, large-volume drug excipients, e.g., larger than about a few millimeters in diameter, of an RTV type silicone rubber base have a strong tendency to depolymerize in the interior, resulting in reduced mechanical strength of the entire vehicle. In order to improve the mechanical properties it has been proposed to suspend fillers, e.g., highly dispersed silicon dioxide and the like, in the elastomer. However, the fillers often absorb the effective drug agent and thus impair the uniformity of drug release from the carrier material, and each drug-filler combination must be separately evaluated. The release of effective drugs from RTV-vulcanizates takes place in many cases at such high rates, as compared to the rates of release from heat-cured silicone rubber vulcanizates, that the formulation of excipients for the uniform release rate of the effective drug over a long term is impossible.

OBJECTS OF THE INVENTION

Accordingly, it is an object of this invention to provide new and improved elastomers useful as drug excipients.

Another object of this invention is to provide sustained release pharmaceutical compositions having an improved excipient as the matrix for a pharmaceutically active ingredient and a process for their preparation.

A further object of this invention is to provide drug implants which exhibit a uniform rate of drug release over a long period of time.

An additional object of this invention is to provide a process for maintaining a uniform drug concentration in a living animal over an extended period of time with a single dosage.

Upon further study of the specification and appended claims, further objects and advantages of this invention will become apparent to those skilled in the art.

SUMMARY OF THE INVENTION

Briefly, the above and other objects are attained in accordance with one aspect of this invention by providing a vulcanizable composition capable of being catalytically cured with a noble metal-based vulcanization catalyst in the presence of a pharmaceutically active amount of a nonionic, lipophilic drug to form a nontoxic elastomeric sustained release pharmaceutical composition, said vulcanizable composition consisting essentially of:

(a) 85-95 parts by weight of a LTV linear dimethylpolysiloxane polymer having a molecular weight of 20,000-50,000, containing an average of 1.98-2.02 monovalent hydrocarbon residues per silicone atom and no more than 0.5 molar percent methylvinylsiloxane units; and (b) correspondingly 15-5 parts by weight of a cross-linking composition consisting essentially of a dimethylpolysiloxane cross-linking agent having a molecular weight of 500-1,000 and containing 1-3 Si—H bonds per molecule.

DETAILED DISCUSSION

It has now surprisingly been found that drug excipients which exhibit a regularly uniform, prolonged release of effective agent are obtained by using a low temperature vulcanizing (LTV) silicone elastomer as the excipient.

The drug excipients of this invention provide a readily introducible, easily retainable, and simply removable source of continuously administered drugs having an uninterrupted useful effect on humans and animals. With the aid of these drug excipients, it is possible to continuously administer drugs in a uniform dosage during specific medication times.

The LTV silicone elastomers suitable for use in the present invention are obtained from linear alkenyl-containing organopolysiloxanes by vulcanization with organo-polysiloxanes containing Si—H bonds at an elevated temperature, i.e., 20°-200° C., preferably 40°-120° C. in the presence of noble metal catalysts, e.g., platinum and platinum compounds. The vulcanized product is either pure elastomer or elastomer containing organosiloxane resin, depending on the type and number of functional groups in the organopolysiloxanes.

Although vulcanization of the linear organopolysiloxanes in the presence of noble metal catalysts can be effected at room temperature or body temperature, i.e., 20°-40° C., vulcanization at a slightly elevated temperature is especially advantageous. The vulcanizing time of the catalyzed mixture is one to six hours at 40°-120° C.

Other LTV silicone elastomers suitable for use in the present invention and their methods of preparation are known in the art and have been described, inter alia in U.S. Pat. No. 2,823,218; U.S. Pat. No. 2,970,150; German Published Application Nos. 1,066,737; 1,171,614; 1,297,335 and 1,570,686. the contents of which are incorporated by reference herein. The LTV silicone elastomers are prepared by curing a LTV linear dimethylpolysiloxane containing methylvinyl groups with a lower molecular weight dimethylpolysiloxane containing Si—H groups using a noble metal-based catalyst. A preferred mixture is one formed from 85-95 weight percent, preferably 89-91% of a linear dimethylpolysiloxane containing no more than about 0.5 molar percent and at least 0,05 molar percent, preferably 0,1-0,5 molar percent of methylvinylsiloxane units, and having a molecular weight of 20,000-50,000, perferably 25,000-45,000.

The cross-linking composition comprises correspondingly 15-5 weight percent, preferably about 11-9 weight percent of the curable mixture and is preferably a dimethylpolysiloxane having an average molecular weight of 500-1000, being substantially free of methylvinylsiloxane units, and containing 1-3 Si—H bonds, preferably 2 or 3 Si—H bonds per molecule. If desired, a portion of the cross-linking composition, e.g., 5-10% based on the total two-component mixture, can comprise a dimethylpolysiloxane resin having a molecular weight of 10,000-40,000, preferably 20,000-30,000 and having at least 0,2 and no more than 1.5, preferably 0,5-1,2 molar percent of methylvinylsiloxane units to enhance cross-linking. The mixture is catalytically vulcanized with a catalytic amount, i.e., $10^{-2}$–$10^{-10}$, preferably $10^{-3}$–$10^{-8}$ molar parts of a noble metal catalyst, preferably platinum and especially hexachloroplatanic acid by heating to an elevated temperature, i.e., 20°-200° C. for a period of time sufficient to complete vulcanization into a cured elastomer; details can be found in the aforementioned incorporated references.

The location of the ethylenic linkages in the linear dimethylpolysiloxane is not substantial, both terminal and non-terminal unsaturated groups are reactive.

The Si—H bonds containing silicon compound described above reacts with any unsaturated bond of a compound containing at least one pair of aliphatic carbon atom linked by multiple bonds, i.e., any compound containing ethylenic or acetylenic bonds, or with any mixture of such compounds. The presence of other substituents in the molecule, whether they are functional or entirely inert, does not prohibit the reaction.

The curing reaction proceeds by the addition of the silicon-hydrogen bond to a pair of aliphatic carbon atoms linked by multiple bonds, i.e., ethylenic or acetylenic.

The vulcanized products are either pure elastomers or elastomers containing organosiloxane resin depending on the type and number of functional groups in the curing agent organosiloxane. They exhibit a Shore A hardness of 51–55 (DIN 53 505).

A desired drug dispensing form with a sustained release of effective agent is obtained by mixing the catalyzed LTV-silicone mixture with one or more drugs followed by vulcanization.

If the drug contains ethylenic or acetylenic linkages, i.e., d-norgestrel, a certain amount of the drug reacts with an unimportant part of the Si—H containing silicon compound depending of the curing temperature, the quantity of the Si—H containing silicon compound and the reactivity of the unsaturated bonds in the drug. This part is negligible for the sustained drug release rate. The enclosed drug behaves inert towards any applied solvent, e.g., body liquids.

By the term constant drug release rate as used herein is meant thus uniform release rate which, over long period of time, enables immediate use of drugs in desired medications without interruptions or variations in the supply.

The term over a long period of time means a time interval of several months or years.

Especially suitable for preparing excipients of the present invention is a dimethylpolysiloxane elastomer containing an average of 1.98–2.02 monovalent hydrocarbon residues per silicon atom and 0,05–0,5, preferably 0,1–0,5 and no more than 0.5 molar percent methylvinylsiloxane units.

The dimethylpolysiloxane LTV elastomer is inactive with respect to nonionic lipophilic drugs; nontoxic; physiologically compatible, and cannot be absorbed by the living organism. They are substantially free of peroxide, acetic acid, metal salts of carboxylic acids which are toxic to a living orgaism and other toxic curing by-products which have severely limited the use of prior art silicone excipients.

The drug excipients of the present invention are suitable as vehicles for one or more nonionic, lipophilic drugs. By the term nonionic as used herein is meant those drugs which, in the condition in which they are to be administered or bound in the excipient matrix of the present invention, exhibit dissociation constants of less than about $10^{-7}$.

By the term lipophilic as used herein is meant those drugs which, in the condition in which they are to be bound in the excipient matrix of the present invention, are soluble or miscible in conventional fat solvents, e.g., ether, chloroform, benzene, etc. The drugs can be bound singly or in admixture and in pure form or with conventional additives. The additives are, e.g., lactose, magnesium stearate, highly dispersed barium sulfate with a particle size smaller than 4 μm and silicon oil with a molecular weight of 300–20,000.

Suitable drugs with which, in a novel effective manner, undesired conditions in or at the human or animal organism are to be treated or controlled and which exhibit these properties include but are not limited to hormones, e.g., cyproterone acetate, progesterone, estradiol, testosterone, insulin, trijodthyronin, cortisone;

prostaglandins, e.g., prostaglandine $E_1$, prostaglandine $E_2$, prostaglandine $A_1$ and prostaglandine $F_{2\alpha}$;

vitamins, e.g., vitamin A, vitamin $D_2$, vitamin $D_3$, vitamin E, vitamin $K_1$, vitamin $K_2$ and derivatives of vitamin $B_1$, e.g., thiamine tetrahydrofurfuryl disulfide or thiamine propyldisulfide; antibiotics, e.g., erythromycin and tetracycline;

contraceptives, e.g., chlormadinone, chlormadinone acetate, megestrol acetate, d-norgestrel, medroxyprogesterone acetate and spermicides, e.g., p-diisobutylphenoxypolyethoxyethanol.

The drugs are employed in at least the pharmaceutically active amounts known in the art, preferably in a 1,000 fold excess.

The drug excipients of the present invention are unique in that, due to their special molecular structure, they dissolve nonionic, lipid-soluble drugs in unusually high concentrations, i.e., typically 0,05–3,0 gm % and often 0,1–2,5 gm %. Aqueous soluble ionic drugs cannot be sufficiently dissolved in the drug excipients of the present invention. The drug excipients are capable of releasing the matrix-bound drugs in precisely controllable amounts, even at minimum dosages, in a uniformly delayed (release) manner, whereby a uniform and constant drug level is deposited and maintained in a living organism during a predetermined time interval for which the pharmaceutical effects are desired, e.g., several months.

A further important feature of the drug excipients of this invention resides in that the geometrical form of shaped objects prepared therefrom can be determined almost exclusively by the type and amount of effective drug to be administered, the desired rate of release of the drug from the vehicle, and the site of application. Accordingly, their configuration can be determined arbitrarily since the vulcanization of the organopolysiloxanes employed according to this invention is independent of moisture and atmospheric oxygen and can be conducted in closed molds.

The desired medicines are produced from the excipient material by mixing the elastomeric raw material with a desired drug followed by vulcanization at an elevated temperature, preferably at 40°–120° C. The thusly-prepared medicines are either constructed entirely or partially according to the matrix principle or represent effective drug solutions in the elastomer.

However, medicines can also be made comprising a core containing a high concentration of the effective agent and an outer silicone elastomer casing of any desired layer thickness having a low concentration of effective agent; conversely, the medicines can comprise a core piece having a low concentration of effective agent surrounded by a drug-elastomer layer of effective agent. The variation in concentration of effective agent between the high and low concentration layers can be one hundred fold or higher, but is generally 1 to 60 fold, preferably 10 to 50 fold. An envelope with a low content of effective agent encasing a drug-enriched core in which the effective agent is predominantly suspended is obtained, e.g., by a brief and incomplete alcohol extraction of drugs built up according to the matrix principle. The drugs can also be produced in the form of a prosthetic device for the body, from which the effective agent is sustained released in a predetermined manner. If necessary or desirable, it is also possible to inject catalyzed elastomer raw material-drug mixtures and to complete the vulcanization in vivo at the predetermined site of effectiveness. In carrying out the vulcanization in vivo, catalyzed silicone-drug mixtures are conventionally injected within the predetermined tissue of the body using a syringue with a cannula for viscous solutions.

The excipient can be provided for special applications with a retrieving string of a suitable material, e.g., surgical silk, and introduced as an implant into a suitable applicator.

The excipient can also be made of a core enriched in effective drug and further comprising an auxiliary agent or agents which are not markedly soluble in the silicone elastomer or which effect the release of the effective agents from the drug vehicles to the desired extent, together with and a superimposed LTV-silicone elastomer envelope which can have a higher, lower or similar content of effective agent.

The medicines of this invention can be implanted at the affected organ, or also at other parts of the body where a drug-evoked effect is desired. For a accurate localization in the body, the implant can also contain a small amount of barium sulfate to enhance X-ray contrast.

By means of the excipient of this invention, many effective drug agents can be successfully employed which have heretofore been unusable with prior art excipient or carrier materials in suitable drug preparations, e.g., for the intrauterine or intravaginal application of drugs.

The drug excipient of this invention can also be utilized to introduce and maintain a base line of the effective agent, which can be supplemented to a temporarily higher dosage by conventional oral or parenteral applications.

The effective drugs can be contained in the vehicle either in dissolved or suspended form. Solids are normally more chemically stable than solutions and thus can be advantageously applied directly to the site of administration. For the preparation of a suspension, the effective drug agents are preferably processed in a dry, pulverized condition so that they are uniformly distributed in the carrier material and are predominantly suspended in the granular size optimal for the intended purpose of application, or somewhat compressed and surrounded by the elastomer. The higher the water solubility of the effective drug, the larger is the selected size of the granular particles. The particle size is advantageously 2–500 $\mu$m, preferably 4–400 $\mu$m.

When it is desired to administer physiologically highly effective agents released in extremely uniform, extraordinarily small quantities by the excipient carrier material, the excipient is produced so that the effective drug is contained therein exclusively in the dissolved form.

The drug excipients according to this invention can be conventionally sterilized in saturated, pressurized steam at 120° C. without incurring any undesired changes.

The medicines made of LTV-silicone elastomer according to this invention have a Shore A hardness (DIN 53 505) of 45–70. Accordingly, they do not crumble upon mechanical stress and are less susceptible to damage by handling with metallic instruments during their introduction into the organism in comparison with RTV-elastomer excipients of the prior art, to which must often be added fillers with their disadvantageous drug absorption properties in order to improve the mechanical characteristics of the medicine.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the following Examples, the temperatures are set forth in degrees Celsius; unless otherwise indicated, all percentages are by weight.

The terms "curing"; "vulcanizing"; "crosslinking", etc., are used interchangeably herein to refer to process by which the plastic organopolysiloxane is converted to a relatively elastic rigid product by the formation of chemical bridges between the polysiloxane claims.

EXAMPLE 1

A suspension free of air bubbles is prepared from 0.8 g. of extremely finely micronized cyproterone acetate with 9.2 g. of LTV-silicone rubber two-component material (produced, for example, according to U.S. Pat. No. 2,823,218 and consisting of 89–91% linear dimethylpolysiloxane containing maximally 0.5 molar percent of methylvinylsiloxane units; and 9–11% dimethylpolysiloxanes having a molecular weight of 500–1000 and containing up to 3 Si—H bonds per molecule) and are catalyzed with platinum or platinum compounds, such as hexachloroplatinic acid. The suspension is poured into molds representing cylinders with hemispheres attached at the ends and having a total length of 6 mm., a cyclindrical diameter of 5 mm., and a radius of curvature of the hem spheres of 2.8 mm., and vulcanized by heating for 5 hours to 100° C. Drug excipients built up according to the matrix principle are thus obtained which contain cyproterone acetate predominantly in the microcrystalline form. After steriization under compressed steam at 120° C. for one hour, they exhibit a Shore A hardness of 53–55 and are intended for implantation.

EXAMPLE 2

A suspension free of air bubbles is obtained by pasting 10.0 g. of micronized progesterone together with 90.0 g. of LTV-silicone rubber two-component substance comprising 85–89% dimethylpolysiloxane of a resin component containing maximally 0.5 molar percent of methylvinylsiloxane units; 5–6% of a dimethylpolysiloxane cross-linking component with Si—H bonds; and 5–10% of a dimethylpolysiloxane resin with maximally 1.2 molar percent of methylvinylsiloxane units having a cross-linking and reinforcing effect, catalyzed with a platinum-ethanol complex compound). This suspension is poured into molds representing cylinders with hemispheres attached at the ends and having a total length of 8 mm., a cylinder diameter of 5.5 mm., and a radius of curvature of the hemispheres of 3.0 mm., and vulcanized by heating to 80° C. for 5 hours. Thereafter, the progesterone vehicles are extracted for one hour at room temperature with 96% ethanol. The excipients, after one hour of sterilization in pressurized steam at 120° C., exhibit a Shore A hardness of 75-58 and are intended for implantation.

EXAMPLE 3

5.0 g. of megestrol acetate of a particle size of 100μ on the average is pasted into a suspension free of air bubbles together with 95.0 g. of LTV-silicone rubber two-component substance as described in Example 1. The suspension is pressed into cylindrical molds having a diameter of 2.5 mm. and a length of 4 mm. with surgical suturing silk thread of a thickness of 1.5–4 EP I (European Pharmacopoeia I) being inserted therein; this thread forms a loop of a length of 8 cm. outside of the mold, intended as a retrieving string. The composition is vulcanized by heating to 100° C. for three hours. The thus-obtained vulcanizates are centered, by means of the inserted retrieving threads, in cylindrical molds having a diameter of 3.5 mm. and a length of 6 mm. The hollow space remaining in the molds is filled with an LTV-silicone rubber two-component composition free of air bubbles. By heating to 100° C. for three hours, the envelope free of medicinal agent is vulcanized on the silicone elastomer vehicle containing megestrol acetate. The drug excipients, after being heated for one hour under pressurized steam to 120° C., exhibit a Shore A hardness of 51–53 and are intended for intrauterine application.

EXAMPLE 4

2.0 g. of extremely finely micronized d-norgestrel is pasted together with 98.0 g. of LTV-silicone rubber two-component composition as described in Example 2. The suspension is placed under a vacuum of 200 mm. Hg for one hour and then pressed into cylindrical molds having a diameter of 3.5 mm. and a length of 8 mm. with a centrally inserted thread of surgical silk having a fiber thickness of 2 EP I, this thread having a length of 6 mm. within the mold and a length of 10 cm. outside of the mold. The suspension is vulcanized by heating for two hours to 120° C. In this way, drug excipients are obtained which contain d-norgestrel in the dissolved form and which are intended for intrauterine administration after sterilization under pressurized steam.

EXAMPLE 5

A suspension of 15.0 g. of extremely finely micronized cyproterone acetate and 5.0 g. of finely precipitated barium sulfate in 80.0 g. of the LTV-silicone rubber two-component composition described in Example 1 is vulcanized in biconvex molds having a length of 18 mm., a width of 10.5 mm., and a maximum thickness of 4 mm., by heating for 3 hours to 120° C. The vulcanizates are sterilized for one hour under pressurized steam at 120° C. and represent drug excipients for implantation.

EXAMPLE 6

Under aseptic conditions, 10.0 g. of sterilized, extremely finely micronized d-norgestrel is worked into a uniform suspension with 81.0 g. of an aseptically filtered dimethylpolysiloxane containing methylvinylsiloxane groups as a component of the LTV-silicone rubber two-component substance disclosed in Example 1. Respectively 0.9 ml. of this suspension and 0.1 ml. of the likewise aseptically filtered second component of the LTV-silicone rubber two-component composition (platinum catalyst in a mixture with the dimethylpolysiloxane containing Si—H-bonds) are filled, after a one-hour evacuation under a vacuum of 200 mm. Hg, into two-chamber injection syringes. The two components of the preparation processed in this manner can be mixed shortly prior to the intended injection; the catalyzed, drug-containing suspension is vulcanized in the organism at the predetermined location.

EXAMPLE 7

15.0 g. of cyproterone acetate of an average particle size of 100μ is processed into a homogeneous suspension together with 85.0 g. of LTV-silicone rubber two-component substance as described in Example 1. This suspension is charged into molds representing cylinders with hemispheres attached to the ends and, with a radius of curvature of the hemisphere of 2.8 mm., having a cylindrical diameter of 5.5 mm. and a total length of 15 mm. In these molds, the mixture is vulcanized by heating to 120° C. for three hours. The vulcanized products are extracted with 96% ethanol at room temperature for two hours. After removing the ethanol adhering to the vulcanizates by drying, the drug excipients are sterilized under pressurized steam at 120° C. for one hour, thus obtaining excipients with an envelope of low cyproterone acetate content on a core enriched with cyproterone acetate, intended for implantation.

EXAMPLE 8

A mixture of 10.0 g. of extremely finely micronized d-norgestrel with 14.8 g. of lactose and 0.2 g. of magnesium stearate is compresed in a conventional manner in a tabletting press to biconvex tablets having a weight of 25 mg., a diameter of 3 mm., and a radius of curvature of 3 mm. The tablets are filled into metallic molds preheated to 120° C., representing cylinders with hemispheres attached to the ends having a radius of curvature of 3 mm., a diameter of 6 mm., and a total length of 8 mm., together with the LTV-silicone rubber two-component composition described in greater detail in Example 1. Due to the fact that the onset of vulcanization of the LTV-silicone rubber substances takes place rapidly, the tablet core can be satisfactorily centered within the mold. The LTV-silicone rubber composition is then vulcanized in the molds by heating to 120° C. for two hours. The vulcanizates are sterilized by heating at 120° C. for one hour under pressurized steam. The thus-produced drug excipients are suitable for implantation.

EXAMPLE 9

A suspension free of air bubbles is produced in a conventional manner from 10.0 g. of extremely finely micronized d-norgestresl, 50 mg. of estradiol, and 89.95 g. of one of the two-component compositions of LTV-silicone rubber described in Example 1. By vulcanization at 110° C. for 3 hours, vaginal caps having a diameter of 3 cm., a layer thickness of 0.3 cm., with a radius of curvature of 1.5–1.8 cm., a height of 2 cm., and a central bore of 8 mm. diameter are manufactured from this suspension; these caps contain the d-norgestrel in a uniformly suspended form and estradiol dissolved in the elastomer.

EXAMPLE 10

A uniform suspension free of air bubbles is prepared from 5.0 g. of extremely finely micronized estradiol and 95.0 g. of the LTV-silicone rubber two-component substance described in Example 1. This suspension is poured in a layer thickness of maximally 1 mm. and in an amount of about 200–300 mg. on the side of a dental prosthesis facing the palate, after degreasing the actual prosthesis material, and vulcanized by heating to 100° C. for two hours.

EXAMPLE 11

A uniform suspension free of air bubbles is produced from 10.0 g. of microcrystalline 2,5-bis(ethylenimino)-3,6-bispropoxy-1,4-benzoquinone with 90.0 g. of the LTV-silicone rubber two-component substance disclosed in Example 1. The suspension is poured into molds representing cylinders with hemispheres attached to the ends having a radius of curvature of 2.8 mm., a cylindrical diameter of 6.0 mm., and a total length of 15 mm. and vulcanized by heating to 80° C. for 5 hours. The sterilized drug excipients are introduced, under aseptic conditions, into a presterilized suitable applicator and are suitable for implantation into the bone marrow of hip bones.

EXAMPLE 12

A homogeneous suspension free of air bubbles is produced from 10.0 g. of extremely finely micronized d-norgestrel and 90.0 g. of the LTV-silicone rubber two-component composition set forth in Example 1. The suspension is poured into molds representing cylinders with hemispheres attached to the ends and having a total length of 15 mm., with a radius of curvature of the hemispheres of 2.8 mm. and a cylinder diameter of 6 mm., with a stainless steel thread of a diameter of 0.3 mm. being inserted in the molds and extending from the molds at the cylindrical ends for a length of about 3 cm. By heating the suspension to 120° C. for three hours, drug excipients are obtained which are affixed in the oral cavity by means of fixed braces as customary in orthodontics for use as jaw-correcting devices, by means of the stainless steel wires attached thereto.

EXAMPLE 13

A homogeneous suspension free of air bubbles is prepared from 3.0 g. of extremely finely micronized d-norgestrel having a particle size of $2\mu$ to maximally $12\mu$, together with 7.0 g. of the LTV-silicone rubber two-component substance disclosed in Example 1. The suspension is molded into cylinders with hemispheres adjoining the ends. The molded articles have a total length of 6 mm., a cylinder diameter of 5 mm., and a radius of curvature of the hemispheres of 2.8 mm.; they are vulcanized by heating to 110° C. for two hours and are then sterilized for one hour at 120° C. under pressurized steam. The vulcanizates containing d-norgestrel represent drug excipients constructed according to the matrix principle and are intended for implantation.

EXAMPLE 14

An air-bubble-free, homogeneous suspension is obtained from 10.0 g. of micronized testosterone having a particle size of about $4-12\mu$, together with 10.0 g. of the LTV-silicone rubber two-component composition described in Example 2. This suspension is molded into capsules representing cylinders with hemispheres attached to the ends. The capsules, having a total length of 22 mm., a cylinder diameter of 9.5 mm., and a radius of curvature of the hemispheres of 4.8 mm., are then sterilized by heating to 120° C. for two hours under pressurized steam. The testosterone capsules are intended for subcutaneous implantation.

EXAMPLE 15

A suspension containing 50% by weight of testosterone of a particle size of $4-12\mu$ in the LTV-silicone rubber two-component composition set forth in greater detail in Example 1 is rolled into sheets having a layer thickness of 1 mm.; these sheets are vulcanized by heating to 100° C. for three hours. Testosterone-containing strips from these sheets, having the dimensions of $15\times30$ mm., are mounted centrally on polyamide films coated unilaterally with a polyacrylate adhesive and having the dimensions of $25\times45$ mm., and the still vacant adhesive film, as well as the opposite side of the testosterone sheets are provided with an easily removable cover strip overlapping in the middle. The polyacrylate adhesive composition employed is preferably a copolymer of acrylic acid and isooctyl acrylate in a molar ratio of about 6:94, as disclosed in DAS No. [German Published Application] 1,263,989.

In long-term applications of plasters of this type, the testosterone is to exert a systemic effect after absorption through the skin.

EXAMPLE 16

6.0 g. of micronized D-norgestrel is processed with 4.0 g. of LTV silicone rubber two-component composition, as described in Example 1, into a suspension free of air bubbles. This suspension is shaped into thread material having a diameter of 0.5 mm. and vulcanized by heating for two hours to 110° C. This thread material, containing the medicinal agent, is worked, together with cotton fiber, as used for the production of surgical cotton, into a fabric having a width of 2 cm. and a length of 2.5 cm. with a linen binding, which is intended for intravaginal application. The fabric has, in the warp, a thread density of 12 threads per cm. with a thread thickness of the cotton yarn of 17 g./1000 m., wherein each third thread is a silicone elastomer thread containing the medicinal agent. In the weft, the fabric has a thread density of 8 threads per cm. with a thread thickness of 14 g./1000 m. The fabric is provided in the warp additionally with a cotton thread having a thickness of 2 mm., which is provided as the retrieval cord.

EXAMPLE 17

Thread material on LTV silicone rubber basis and containing a medicinal agent is produced, as described in Example 16, with the use of micronized progesterone. The thread material is processed into a piece of fabric with linen binding having a width of 2 cm. and a length of 2 cm. and containing 6 threads in the warp and 4 threads in the weft per cm. A layer of a thickness of 0.1 cm., consisting of cellulose wadding, is placed on both sides of this fabric. The drug-containing fabric and the wadding layers are joined by a cotton thread having a diameter of 1.5 mm. which is woven into the piece in the longitudinal direction centrally and simultaneously fashioned as the retrieval cord. The entire system is rolled into a vaginal tampon having a length of 2 cm. and a diameter of 1.2 cm.

EXAMPLE 18

A suspension, free of air bubbles, of 55 parts by weight of micronized $11\beta,17\alpha,21$-trihydroxy-4-pregnene-3,20-dione (hydrocortisone) in 45 parts by weight of LTV silicone rubber two-component composition, as described in Example 2, is shaped into thread material having a diameter of 0.3 mm. By heating for 90 minutes to 110° C., the suspension is vulcanized. With the use of this thread material containing the medicinal agent and cotton thread having a yarn thickness of 17 g./1000 m., a fabric is produced in the form of yard goods which can be used as medical dressing material. This fabric with linen binding has, in the warp, alternatingly 4 cotton threads and one silicone elastomer thread containing an active ingredient, in total 10 threads per cm., and in the weft, alternatingly respectively 3 cotton threads and one silicone elastomer thread with an active ingredient, in total 8 threads per cm.

EXAMPLE 19

A suspension, free of air bubbles, of 50 parts by weight of micronized 6α-fluoro-11β,21-dihydroxy-16α-methyl-1,4-pregnadiene-3,20-dione (fluocortolone) in 50 parts by weight of LTV silicone rubber two-component composition, as described in Example 1, is used for producing, by shaping and subsequent vulcanization for 2 hours at 110° C., a drug-containing thread material having the diameter of 0.3 mm. From the fluocortolone-containing thread material and cotton thread having a thread thickness of 14 g./1000 m., a fabric with linen binding is produced as set forth in greater detail in Example 18. With the use of this fabric and adhesive films, as customary for the production of adhesive bandages, plasters containing medicinal agent are produced for topical application.

EXAMPLE 20

Under aseptic conditions, 0.5 g. of vitamin $D_3$ (cholecalciferol-cholesterol), extremely finely micronized, are processed with 1.1 g. of an LTV silicone rubber two-component composition, as described in Example 1, into a homogeneous suspension. This suspension is poured, under aseptic conditions, into molds resulting in cylindrical products (length 5 mm., diameter 4 mm.) with rounded corners, which products are then vulcanized by heating for 12 hours to 70° C. The thus-obtained medicinal agent has a Shore A hardness of 51-53 and is intended for implantation.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A nontoxic pharmaceutical composition adapted for implantation into a human or animal body to provide a constant, uniform drug release rate over a time interval of several months or years, said composition being substantially free of peroxide, acetic acid and metal salts of carboxylic acids and consisting essentially of a homogeneous mixture of:
   (a) 85-95 parts by weight of a LTV linear dimethylpolysiloxane resin containing 0.05-0.5 molar percent of methylvinylsiloxane units, having a molecular weight of 20,000-50,000 and containing an average of 1.58-2.02 monovalent hydrocarbon residues per silicone atom;
   (b) correspondingly 15-5 parts by weight of a crosslinking composition consisting essentially of a dimethylpolysiloxane crosslinking agent substantially free of methylvinylsiloxane units, having a molecular weight of 500-1000 and containing 1-3 Si—H bonds per molecule;
   (c) a catalytic amount of a noble-metal based crosslinking catalyst; and
   (d) a pharmaceutically active amount of a nonionic, lipophilic drug dissolved or uniformly suspended in said composition.

2. A composition according to claim 1, wherein said drug is selected from the group consisting of hormones, prostaglandins, vitamins, antibiotics, contraceptives and spermicides.

3. A composition according to claim 2, comprising 89-91% by weight of component (a) and correspondingly 11-9% by weight of said crosslinking agent (b).

4. A composition according to claim 2, wherein component (b) consists essentially of 5-10 parts by weight of said crosslinking agent and 5-10 parts by weight of a dimethylpolysiloxane resin having a molecular weight of 10,000-40,000 and having 0.2-1.5 molar percent methylvinylsiloxane units as a auxiliary crosslinking agent.

5. A composition according to claim 4, comprising 85-89% by weight of component (a); 5-6% by weight of said crosslinking agent; and 5-10% by weight of said dimethylpolysiloxane resin.

6. A composition according to claim 2, wherein the noble metal-based crosslinking catalyst is hexachloroplatinic acid.

7. A shaped object having a Shore A hardness of 45-70 prepared by vulcanizing an air-bubble free composition according to claim 2 at 40°-120° C. for 1-6 hours.

8. A shaped object according to claim 7, wherein said composition comprises 89-91% by weight of component (a) and correspondingly 11-9% by weight of said crosslinking agent (b).

9. A shaped object according to claim 7, wherein said composition comprises 85-89% by weight of component (a); 5-6% by weight of said crosslinking agent; and 5-10% by weight of a dimethylpolysiloxane resin having a molecular weight of 10,000—10,000 and having 0.2-1.5 molar percent methylvinylsiloxane units as an auxiliary crosslinking agent.

10. A vulcanized composition according to claim 2.

11. A vulcanized composition according to claim 3.

12. A vulcanized composition according to claim 4.

13. A vulcanized composition according to claim 5.

14. In a process for preparing a nontoxic pharmaceutical composition having a constant drug release rate over a long period of time and containing a pharmaceutically active amount of a nonionic, lipophilic drug and a pharmaceutically acceptable carrier, the improvement which comprises employing the composition according to claim 1.

15. A process according to claim 14, wherein said drug is selected from the group consisting of hormones, prostaglandins, vitamins, antibiotics, contraceptives and spermacides.

16. A process according to claim 15, wherein said crosslinking catalyst is hexachloroplatinic acid.

* * * * *

UNITED STATES PATENT AND TRADEMARK OFFICE
CERTIFICATE OF CORRECTION

PATENT NO. : 4,230,686

DATED : October 28, 1980

INVENTOR(S) : Gisela Schopflin et al

It is certified that error appears in the above—identified patent and that said Letters Patent is hereby corrected as shown below:

Column 14, line 46: reads "ing a molecular weight of 10,000—10,000 and having"

should read -- ing a molecular weight 10,000—40,000 and having -- .

Signed and Sealed this

Tenth Day of February 1981

[SEAL]

Attest:

RENE D. TEGTMEYER

Attesting Officer

Acting Commissioner of Patents and Trademarks